United States Patent
Ma et al.

[11] Patent Number: 5,453,171
[45] Date of Patent: * Sep. 26, 1995

[54] HEPARIN-SELECTIVE POLYMERIC MEMBRANE ELECTRODE

[75] Inventors: Shu-Ching Ma, Burlington, Mass.; Mark E. Meyerhoff; Victor C. Yang, both of Ann Arbor, Mich.

[73] Assignee: The Board of Regents ... of the University of Michigan, Ann Arbor, Mich.

[ * ] Notice: The portion of the term of this patent subsequent to Aug. 17, 2010 has been disclaimed.

[21] Appl. No.: 107,321

[22] Filed: Aug. 16, 1993

Related U.S. Application Data

[63] Continuation-in-part of Ser. No. 849,218, Mar. 10, 1992, Pat. No. 5,236,570.

[51] Int. Cl.$^6$ .................................................... G01N 27/26
[52] U.S. Cl. ........................... 204/418; 204/403; 435/817; 435/288
[58] Field of Search ................................ 204/418, 403; 435/817, 288

[56] References Cited

U.S. PATENT DOCUMENTS 5,165,952  11/1992  Solomon et al. ............................ 427/2
5,183,549   2/1993  Joseph et al. ........................... 204/418

Primary Examiner—John Niebling
Assistant Examiner—Bruce F. Bell
Attorney, Agent, or Firm—Rohm & Monsanto

[57] ABSTRACT

An anion exchange membrane for ionic macromolecules, specifically heparin, which is formed of a polymeric matrix material and an anion exchange material suitable for heparin detection can be employed in an electrochemical sensor arrangement to directly measure the concentration of heparin ions in blood or blood fluid. Potentiometric response to heparin has been observed with membranes comprising 30–70 wt. % polymeric matrix material, such as polyvinyl chloride, 0.1–12 wt. % quaternary ammonium salt, such as tridodecyl methyl ammonium chloride, and 30–70 wt. % of a plasticizer, such as dioctyl sebacate. Moreover, a solid state sensor employs tridodecyl methyl ammonium chloride (TDMAC) dissolved in a polymeric compound, such as silicone rubber, to form a membrane which is responsive to heparin concentration.

21 Claims, 4 Drawing Sheets

HEPARIN-SELECTIVE POLYMERIC MEMBRANE ELECTRODE

STATEMENT OF GOVERNMENT RIGHTS

This invention was made with government support under Grant No. R29-HL38353 awarded by the National Institutes of Health. The government has certain rights in the invention.

RELATIONSHIP TO OTHER APPLICATION

This application is a continuation-in-part of U.S. Ser. No. 07/849,218, filed Mar. 10, 1992, now U.S. Pat. No. 5,236,570 issued on Aug. 17, 1993, the disclosure of which is incorporated herein by reference.

BACKGROUND OF THE INVENTION

This invention relates generally to a polymer membrane type ion-selective electrode, and more particularly, to a polymer membrane type ion-selective electrode suitable for monitoring polyionic macromolecules such as heparin.

Polymer membrane type ion-selective electrodes are now routinely used in commercial biomedical instruments to measure accurately levels of clinical important small ions, such as $Ca^{++}$, $Na^+$, $K^+$, $Li^+$, $H^+$, and $Cl^-$, in undiluted whole blood. These ion-selective electrodes typically comprise a highly plasticized polymeric matrix material with an ion-exchange material or ion-complexing agent therein. The ion-exchange material may be a quaternary ammonium salt, such as tridodecyl methyl ammonium chloride (TDMAC).

Polyvinyl chloride (PVC) is a common polymeric membrane matrix material used in the art of solid-state or liquid-membrane electrodes for the detection of small ions (see, for example, U.S. Pat. No. 4,861,455 or Hartman, et al., "Chloride-Selective Liquid-Membrane Electrodes Based on Lipophilic Methyl-Tri-N-Alkyl-Ammonium Compounds and Their Applicability to Blood Serum Measurements," *Mikrochimica Acta* [Wein], 1978 II 235-246).

Efforts to develop similar sensors, including immuno-based biosensors, for the detection of large biomolecules, such as proteins or drugs, have thus far been unsuccessful. One of the most difficult problems has been identifying appropriate complexing agents and membrane chemistries that yield significant, specific and reversible electrochemical responses to the desired analyte. Even if a specific complexing agent is identified for a macromolecular biomolecule, whether the interaction with the macromolecular ion is strong enough to overcome the rather low mobility of a large ion to yield to significant electrochemical response remains in question. In theory, the sensitivity and selectivity of an ion-selective electrode membranes is governed by both the mobility of the analyte ion and the strength of the interaction between the ion-complexing agent and the analyte ion. In addition, strong interference resulting from a high concentration of small ions, such as chloride ions, in a blood sample may dictate the membrane's response.

An analyte of particular clinical significance is heparin, a polyanionic macromolecule. Heparin is the anticoagulant drug used universally in surgical procedures and extracorporeal therapies, and for the prevention of thromboembolism following surgery or childbirth. Heparin is a group of polydisperse (molecular weight ranges from 5,000 to 30,000 daltons) straight-chain anionic mucopolysaccharides called glycosaminoglycans having an average molecular weight of 15,000 daltons. Glycosaminoglycans are copolymers of sulfated ($SO_3$) and unsulfated uronic/iduronic acids alternating with glucosamine residues.

The major side effect of heparin administration is bleeding. In fact, a survey by the Boston Collaborative Drug Surveillance Program on drug-related deaths among inpatients indicted that heparin is the drug responsible for a majority of drug deaths in reasonably healthy patients. In view of this morbid potential, there is a great need for a means to continuously and accurately measure heparin levels in the bloodstream during surgical procedures. Unfortunately, there currently is no method suitable for direct and rapid determination of the physiological heparin levels. Presently available heparin assays, such as the Activated Clotting Time, are all based on blood clotting time. Further, the prior art assays are not specific to heparin and lack speed, accuracy, consistency, and a defined biochemistry. Further, since the clotting time based heparin assays can not directly measure the blood heparin level, the role of heparin in the associated bleeding complications and the mechanism of the "heparin rebound" phenomenon have never been identified. There is, therefore, a need for a means of directly measuring the levels of heparin in the blood in both clinical practice and medical research.

The quaternary ammonium salt TDMAC is known to bind or complex with heparin. In fact, it is well-known in the medical arts to fabricate thromboresistant biomaterials by heparinizing the surface of a TDMAC-coated or impregnated polymer. TDMAC shares significant structural similarity to polybrene, a synthetic polyquarternary ammonium salt, considered to be one of the most potent heparin antagonists. Although TDMAC has been used as the anion-exchange material in conventional membrane electrodes for the detection of small ions, the art is totally devoid of any suggestion that macromolecules, such as heparin, could be directly detected with TDMAC-doped PVC or silicone rubber membranes.

It is, therefore, an object of this invention to provide an electrochemical sensor for ionic macromolecules.

It is another object of this invention to provide an electrochemical sensor for direct measurement of heparin in whole blood or plasma.

It is also an object of this invention to provide an electrochemical sensor for direct measurement of heparin in whole blood or plasma which is accurate over the expected clinically relevant concentration range.

It is a further object of this invention to provide an electrochemical sensor for direct measurement of heparin in whole blood or plasma which possesses adequate dynamic response characteristics, i.e., responds rapidly to a change in ion concentration and returns promptly to baseline, so that it is suitable for continuous in vivo monitoring.

It is additionally an object of this invention to provide a polymeric membrane electrode having specific selectivity for heparin macromolecules even in the presence of $Cl^-$ and other artionic impurities.

SUMMARY OF THE INVENTION

The foregoing and other objects are achieved by this invention which provides, an ion-selective electrode membrane consisting of a silicone rubber polymer, and approximately between 0.1–12 weight percent TDMAC, the ion-selective electrode membrane being selective for heparin. Preferably the TDMAC is present preferably in a weight percent of approximately 1.5%.

In a preferred embodiment, the TDMAC is combined with the silicone rubber while the silicone rubber is in a dissolved state. Subsequently, the silicone rubber and the TDMAC dissolved therein are installed as a layer on an integrated circuit chip.

In accordance with a method aspect of the invention, a method of forming a substance-sensitive membrane for a solid state sensor arrangement, the includes the steps of:

dissolving a silicone rubber solution;

adding approximately 1.5 weight percent of TDMAC to the dissolved silicone rubber solution; and applying the silicone rubber solution with TDMAC onto a silicon-based integrated circuit chip.

Prior to performing the step of applying, there is provided the further step of cleaning the silicon-based integrated circuit chip in an alcohol bath, which preferably is a supersonic alcohol bath.

In accordance with a sensor aspect of the invention, an integrated circuit chemical sensor arrangement is provided with an input electrode formed of a conductive material in the vicinity of a region formed of a silicon-based semiconductor material, a permselective membrane having an electrochemical property responsive to heparin and formed of a silicone-based compound is arranged to be in adherence with the silicon-based semiconductor material and in electrical communication with the input electrode, for producing at the input electrode a voltage responsive to the electrochemical property.

In accordance with a further sensor aspect of the invention, an integrated circuit chemical sensor arrangement has, as previously indicated, an input electrode formed of a conductive material in the vicinity of a region formed of a silicon-based semiconductor material, and a permselective membrane. The permselective membrane has a heparin-selective electrochemical property, and is formed of a polymeric compound dissolved in a solvent with TDMAC, whereby the TDMAC is distributed in the polymeric compound, and then removing the solvent. The permselective membrane is then arranged to be in adherence with the silicon-based semiconductor material and in electrical communication with the input electrode, for producing at the input electrode a voltage responsive to a concentration of heparin.

In one embodiment of this aspect of the invention, the conductive material is a silver epoxy which forms an electrical contact having a surface area of approximately 0.41 mm$^2$, and the permselective membrane has an area of approximately 5 mm$^2$. The thickness of the permselective membrane is approximately 150 μm.

In a highly preferred embodiment, the benefits of greatly increased production quantities and reproducibility are achieved by screen printing the permselective membrane onto the silicon-based semiconductor material.

In one embodiment, an anion exchange membrane for ionic macromolecules, specifically heparin, which is formed of a polymeric matrix material and an anion exchange material suitable for heparin detection. The anion exchange material is dispersed or dissolved in the plasticized polymeric matrix material.

PVC or silicone rubber has been found to produce potentiometric response to heparin when used as the polymeric matrix material of the anion exchange membrane of the present invention. Although the examples herein are directed primarily to formulations using PVC or silicone rubber as the polymeric matrix material, it is to be specifically understood that other film-forming, hydrophobic polymers are suitable matrix materials. Various polymeric materials of the type used in electrode membranes can be used including synthetic and natural polymeric materials such as polymers and copolymers of ethylenically unsaturated monomers such as polyethylenes, poly(1,2-butadienes) and the like; polycondensation polymers, such as polyesters, polyamides, polyurethanes, etc. Such various polymers specifically include, without limitation, polyurethane, cellulose triacetate, and poly(vinyl alcohol)/poly(vinylchloride) copolymer. For body-invasive uses, the polymeric matrix material should be biocompatible.

In some embodiments of the invention, one or more plasticizers optionally may be used in the membrane composition in order to maintain homogeneity of the mixture. A particularly preferred plasticizer is dioctyl sebacate (DOS). However, other plasticizers are suitable for preparing anion exchange membranes in accordance with the present invention. Such other plasticizers include, without limitation, isopropyl palmitate, isopropyl isostearate, diisooctyl phthalate, and the other plasticizers listed on Table II below. In selecting a plasticizer for the polymeric membrane, it is important that the plasticizer is compatible with the polymeric matrix material. Incompatibility manifests itself, for example, as exudation of the plasticizer during curing.

The anion exchange material is preferably a quaternary ammonium salt. In particularly preferred embodiments of the invention, the quaternary ammonium salts which produced optimum results are TDMAC and aliquat 336 (trioctyl methyl ammonium chloride). Other quaternary ammonium salts which produce a potentiometric response include, without limitation, trimethyl phenyl ammonium chloride, dimethyl dioctadecyl ammonium bromide, tetramethylammonium, polybrene, and the other quaternary ammonium salts list on Table III below. In addition to quaternary ammonium salts, quaternary phosphonium salts or quaternary arsonium salts may be used in the practice of the invention.

Selectivity and sensitivity are affected by the contents of the polymeric membranes. In preferred embodiments, potentiometric response to heparin has been observed with membranes comprising 30–70 wt. % polymeric matrix material; 30–70 wt. % plasticizer; and 0.1–12 wt. % quaternary ammonium salt. Particularly preferred embodiments comprise about 65 wt. % PVC, about 33 wt. % DOS, and 1.4–2.0 wt. % TDMAC.

In certain preferred embodiments, the anion exchange membrane is prepared as a homogenous solution of the polymeric matrix material, plasticizer, and anion exchange material in a suitable organic solvent, such as tetrahydrofuran (THF) or dimethylformamide (DMF), which is suitable for casting into a thin film. The thin film can be cut to size for mounting on an electrode body as will be described hereinbelow. Typically, the membrane thickness is in the range of about 100 μm to 300 μm, preferably, ~200 μm.

In a specific device embodiment, a membrane electrode of the type having an ion-selective membrane constructed in accordance with the principles of the invention comprises:

(a) a housing for containing a reference solution;

(b) an electrode, such as a Ag/AgCl electrode, arranged in the housing so that it is disposed in the reference solution and is connected electrically to a potentiometer and reference electrode, such as a Ag/AgCl double junction reference electrode; and (b) the heparin-selective membrane of the present invention which is disposed on one end of the housing so as to seal the reference solution inside the housing and to contact a sample solution external to the housing.

In alternative device embodiments, the anion exchange membrane solution may be layered or coated on a conductive metallic substrate or surface, such as a conductive wire.

In a method of use aspect of the present invention, the concentration of heparin in a liquid medium is measured as a function of its potentiometric response using a membrane electrode fabricated in accordance with the principles of the invention. The liquid medium may be a body fluid, such as blood or blood components.

BRIEF DESCRIPTION OF THE DRAWING

Comprehension of the invention is facilitated by reading the following detailed description, in conjunction with the annexed drawing, in which.

DETAILED DESCRIPTION

An understanding of the invention can be enhanced by reference to the following examples of specific embodiments.

EXAMPLE 1

In a particularly preferred specific embodiment, a heparin-selective polymer membrane is prepared which comprises:

1.5 weight percent TDMAC;
65.7 weight percent PVC; and
32.8 weight percent dioctyl sebacate (DOS).

A polymer casting solution is prepared by dissolving 132 mg PVC, 66 mg DOS, and 3–4 mg TDMAC in ~1.5 ml THF solvent. This solution is cast into a glass ring (i.d.=22 mm) on a glass slide. The solvent is permitted to evaporate, illustratively overnight, to form a thin film of ~200 μm in thickness.

Figure 1:
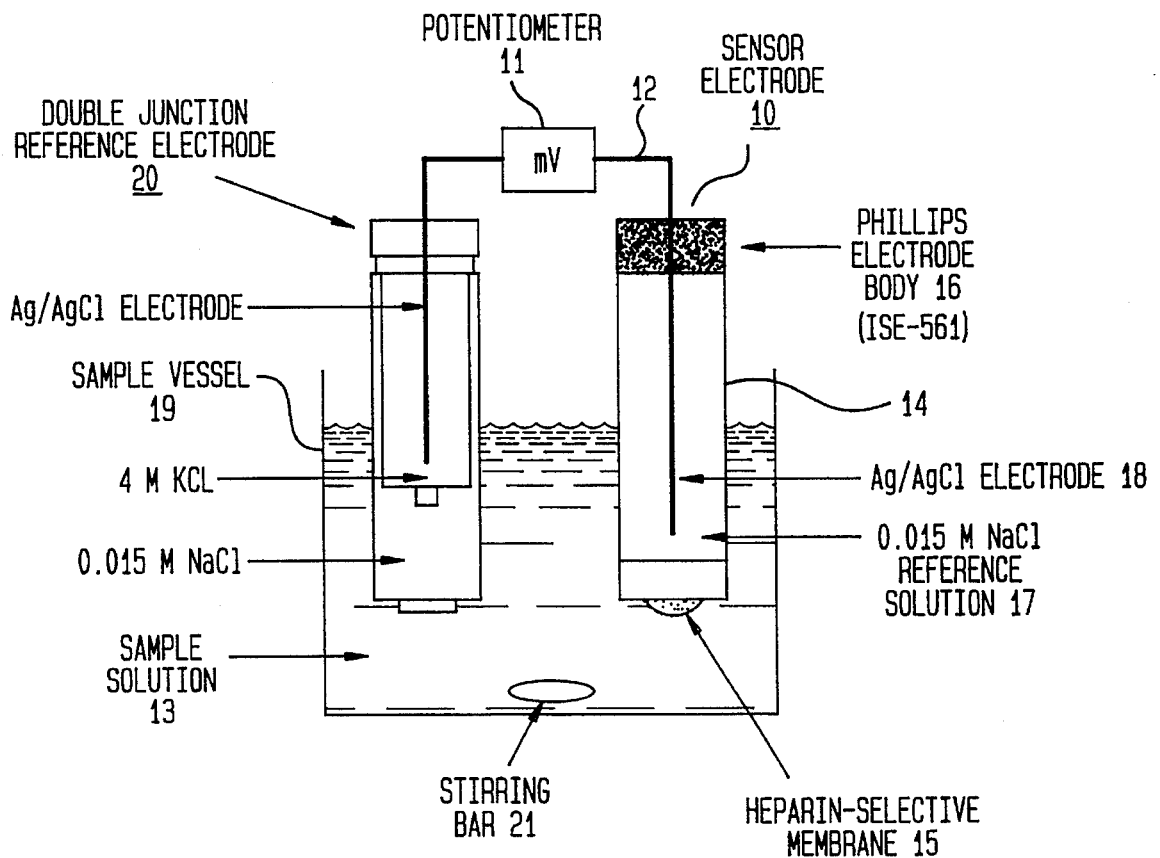
FIG. 1 is a schematic representation of an assembly for the measurement of an analyte solution with a heparin-selective polymeric membrane electrode in accordance with the invention.

FIG. 1 is a schematic representation of an assembly for the measurement of an analyte solution with a heparin-selective polymeric membrane electrode 10. In this embodiment of the invention, a thin heparin-selective polymer membrane 15 constructed in accordance with the principles of the invention is mounted onto the tip of a conventional Philips ISW-561 electrode body 16 (available from Glasblaserei Moller, Zurich, Switzerland). Electrode body 16, includes housing 14 for containing a reference solution 17, in this case 0.015 M NaCl, and a Ag/AgCl electrode 18 which is disposed in reference solution 17 and connected electrically by wire 12 to potentiometer 11 and reference electrode 20, in this case a Ag/AgCl double junction reference electrode.

Referring to FIG. 1, a potentiometric response of an analyte in sample solution 13 contained in sample vessel 19 was measured relative to outer Ag/AgCl double junction reference electrode 20 at ambient room temperature (~22° C.). Sample solution 13 was stirred with a magnetic stirring bar 21 during all experiments.

Figure 2:
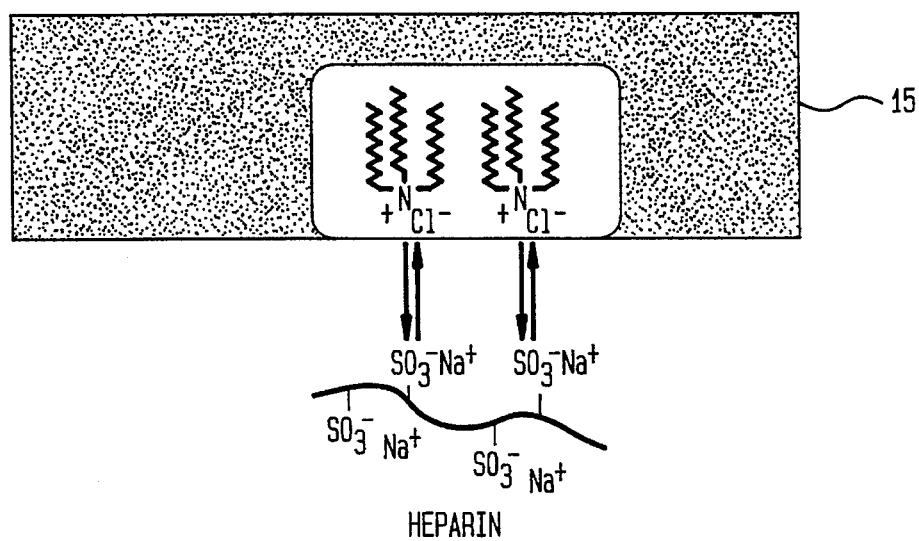
FIG. 2 is a schematic representation of the heparin-selective polymeric membrane and solution interface during operation of the heparin-selective polymeric membrane electrode of FIG. 1.

Heparin-selective polymeric membrane 15 serves as the interface between sample solution 13 and reference solution 17. FIG. 2 is a schematic representation of the heparin-selective polymeric membrane and solution interface during operation of the heparin-selective polymeric membrane electrode of FIG. 1.

Figure 3:
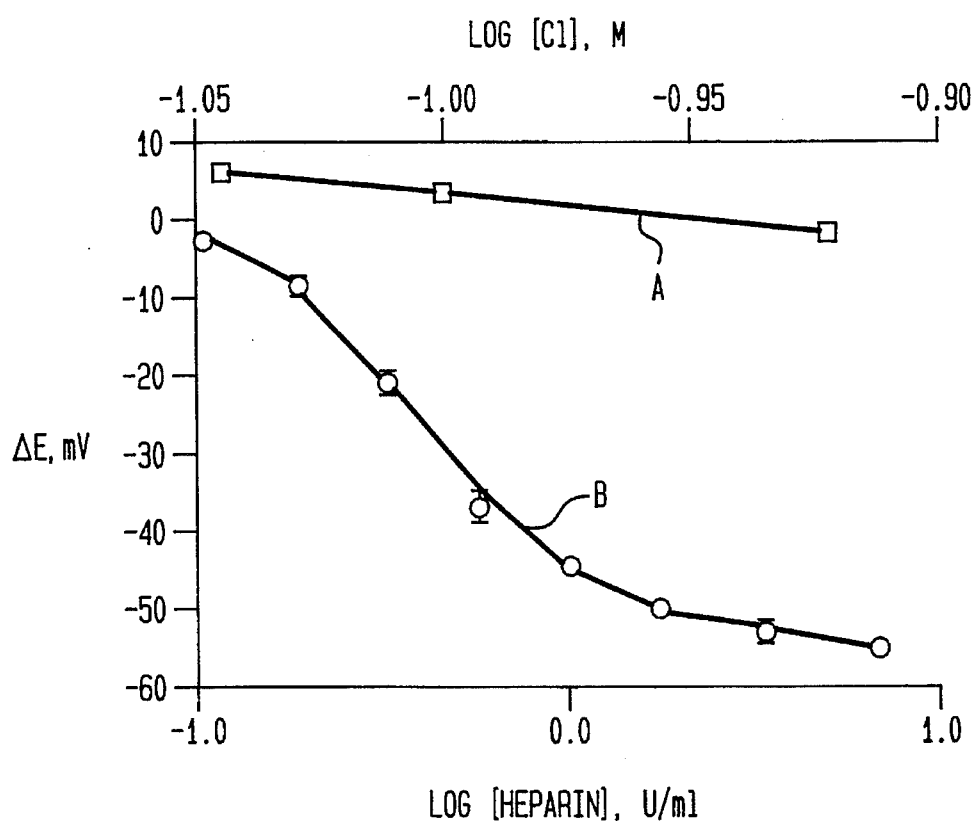
FIG. 3 is a graphical representation of the response characteristics of a heparin-selective electrode to Cl– ions (Line A) and heparin (Line B) over their respective physiological concentration range. The potential change ($\Delta E$) in mV from the original cell potential is plotted against the logarithm of the concentration of the analytes in clinical activity units per ml (U/ml)

FIG. 3 is a graphical representation of the response characteristics of a heparin-selective electrode (as in Example 1) to Cl– ions and heparin over their respective physiological concentration range. $\Delta E$ represents the potential change (i.e., the cell potential) in mV relative to the absolute potential reading in 0.12 NaCl (i.e., without added heparin or varying chloride concentration). $\Delta E$ is plotted against the logarithm of the concentration of the analytes in U/ml. The data were obtained in duplicate from two different electrodes and plotted as the mean ± standard deviation (SD). Referring to FIG. 3, line (A) is the response to solutions of NaCl at concentrations ranging from 0.09 to 0.12M (data points designated as "□") and line (B) is the response to aqueous solutions of heparin and 0.12 M NaCl (data points designated as "O").

Despite the presence of a high level of chloride ions (0.12M) in the sample, the heparin-selective electrode of the present invention exhibited sensitivity to very low levels of heparin in the aqueous solution. A linear region, covering the concentration range from 0.2 to 1.0 U/ml heparin, is observable on FIG. 3, Line (B). Membranes formulated with 30–40% by weight plasticizer exhibit selective potentiometric response to the highly sulfated heparin macromolecule relative to chloride over their respective physiological concentration ranges. The electrode detects low levels of heparin (0.2–1.0 U/ml) even in the presence of 0.12M chloride.

No response was observed to heparin when a thin dialysis membrane (molecular weight cutoff=12,000 daltons) was placed over the outer surface of the polymer membrane to block the heparin-TDMAC interaction. Further, the addition of protamine to a heparin sample immediately shifted the potential of the electrode toward a more positive direction. Protamine is a clinically-used heparin antagonist that binds heparin through electrostatic interaction and thereby decreases the activity of free heparin in the solution. These observations indicate that the heparin-selective electrode of the present invention is responding directly to heparin macromolecules and not to small ionic impurities which might be present in the heparin samples.

Figure 4:
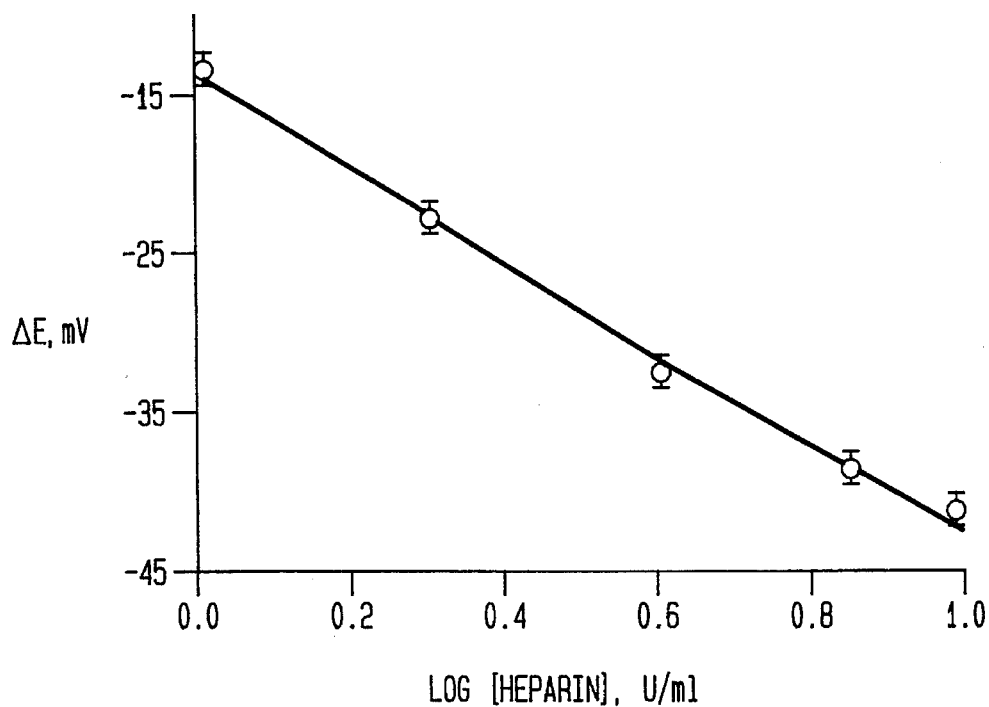
FIG. 4 is a graphical representation of the response characteristics of a heparin-selective electrode to heparin in citrated fresh human plasma samples.

FIG. 4 is a graphical representation of the response characteristics of a heparin-selective electrode to heparin in citrated fresh human plasma samples. The potential change, $\Delta E$, in mV is plotted against the logarithm of the heparin concentration in U/ml. The plot shown in FIG. 4 exhibits a linear relationship ($r^2$=0.99) between the voltage change and the logarithm of heparin concentration over the concentration range tested (1.0 to 9.8 U/ml). The heparin levels encountered in most surgical procedures are within the range of 1.0 to 8.0 U/ml. Thus, the sensitivity of the heparin-selective electrode of the present invention is adequate for clinical purposes.

The response of the heparin-selective electrode to a wide range of related molecular species was measured and the results are shown in Table I. Such related species include the glycosaminoglycan analogs dermantin sulfate (Derm-S), chondroitin sulfate A (Chon-A), and hyaluronic acid (Hya). Other tested species were a highly sulfated anionic polymer, poly(vinylsulfate) (PVS) and sulfated and non-sulfated glucosamine residues (major monosaccharide building blocks of heparin). All tested compounds were prepared in 0.12M NaCl solution at the same concentration (12 μg/ml). For heparin, 12 μg/ml is approximately equivalent to 1.2 U/ml clinical activity. Unless otherwise specified, the compounds were in their sodium salt form.

TABLE I

POTENTIOMETRIC RESPONSE OF THE HEPARIN SENSOR TOWARD VARIOUS COMPOUNDS

| Tested Compounds† (12 μg/ml) | ΔE, m.V.‡ | Sulfate Content (wt %) |
|---|---|---|
| Hep | −50 | 13.0 |
| Derm-S | −25 | 9.0 |
| Chon-A | −10 | 7.0 |
| Hya | 0 | 0 |
| PVS | 0 | 62.0 |
| Glucosamine | 0 | 0 |
| Glucosamine 2-sulfate | 0 | 25.0 |
| Glucosamine 3-sulfate (free acid) | 0 | 27.0 |
| Glucosamine 6-sulfate (free base) | 0 | 27.0 |
| Glucosamine 2,3-disulfate | 0 | 42.0 |

Referring to Table I, the potentiometric response to heparin was superior to the response observed to the other species with reducing response to other glycosaminoglycan analogs in direct correlation with the sulfate content of these compounds. However, the electrode displayed no measurable response to PVS despite the fact that PVS contains up to 62 wt. % sulfate. Likewise, none of the glucosamine residues yielded detectable potentiometric signals. Although not wishing to be bound by any theory, the preferred extraction of heparin to sulfated glucosamine residues may be due to the ability of heparin to interact simultaneously with a large number of immobile positively charged tridodecyl ammonium sites in the hydrophobic membrane (see FIG. 2), whereas the lack of response to PVS may be attributed to the rather hydrophilic nature of PVS that prohibits its extraction by the hydrophobic organic membrane. Previous studies with ion-exchanger based membrane electrodes suggested that the response mechanism involves the extraction of the substrate into the organic membrane phase, and the concomitant ion-pairing of the substrate at the sites of the complexing agent. The equilibrium constant for the ion-exchange extraction appears to dictate the observed electrode selectivity.

EXAMPLE 2

The potentiometric response to heparin for various heparin-selective polymer membrane compositions plasticized with different plasticizers are summarized in Table II below. The compositions of Table II basically comprise 66 mg PVC, ~132 mg plasticizer, and 6 mg Aliquat 336 as the quaternary ammonium salt. The weight percentages of the various components are given in parentheses on the table. The potential response is shown on the table as ΔE (mV) between an aqueous 0.15M NaCl solution and 6.9 U/ml heparin in an aqueous solution of 0.15M NaCl.

TABLE II

POTENTIOMETRIC RESPONSE TO HEPARIN AND COMPOSITIONS OF MEMBRANES COMPOSED OF 66 MG PVC, 132 MG PLASTICIZER AND 6 MG ALIQUAT 336

| Membrane | ΔE 0–6.9 U/ml (in 0.15M NaCl) | Plasticizer | wt % of 66 mg PVC | mg plasticizer (wt %) | wt % of 6 mg aliquat 336 |
|---|---|---|---|---|---|
| a | −30 | Dicapryl adipate | (31.9) | 134.8 (65.2) | (2.9) |
| b | −28.5 | Di-n-hexyl azelate | (31.6) | 136.6 (65.5) | (2.9) |
| c | −18.8 | Dipropylene glycol dibenzoate | (32.3) | 132.6 (64.8) | (2.9) |
| d | −5.7 | Tri-n-butyl citrate | (32.0) | 134 (65.0) | (2.9) |
| e | −29.3 | 2-Ethyl hexyl epoxytallate | (31.9) | 135 (65.2) | (2.9) |
| f | −29.5 | Di(2-ethylhexyl maleate)dioctyl maleate | (32.4) | 132 (64.7) | (2.9) |
| g | −25.5 | Tri-(n-octyl,n-decyl)trimallitate | (32.4) | 132 (64.7) | (2.9) |
| h | −26 | Methyl oleate | (32.2) | 133.2 (64.9) | (2.9) |
| i | −42.9 | Isopropyl palmitate | (31.9) | 135 (65.2) | (2.9) |
| j | −0.3 | t-Butyl phenyl diphenyl phosphate | (34.4) | 137 (65.6) | (2.9) |
| k | −28.1 | Butyl octyl phthalate | (32.4) | 131.5 (64.6) | (2.9) |
| l | −32.7 | Diisooctyl phthalate | (31.9) | 135.2 (65.3) | (2.9) |
| m | −27.6 | Glyceryl triacetyl ricinoleate | (32.3) | 132.4 (64.8) | (2.9) |
| n | −25.2 | Dibutyl sebacate | 32.1 | 133.8 (65.0) | (2.9) |
| o | −49.6 | Isopropyl isostearate | 32.2) | 133 (64.9) | (2.9) |
| p | −40.4 | Dioctyl sebacate | 32.3) | 132.6 (64.8) | (2.9) |
| q | −29.4 | Dioctyl phthalate | (32.0) | 134.2 (65.1) | (2.9) |
| r | −10.4 | Dibutyl phthalate | (32.1) | 133.9 (65.0) | (2.9) |
| s | −12.4 | o-Nitrophenyl octyl ether | (31.7) | 136 (65.4) | (2.9) |

Table II demonstrates that significant potentiometric responses can be achieved in PVC membranes plasticized with various plasticizers. Particularly outstanding responses were observed with membranes (i), (o), and (p).

EXAMPLE 3

The potentiometric response of various heparin-selective polymer membrane compositions doped with different quaternary ammonium salts are summarized in Table III below. The compositions of Table III basically comprise 66 mg PVC, ~132 mg DOS, and 6 mg quaternary ammonium salt. The weight percentages of the various components in the resulting membrane are given in parentheses on the table. The potential response is shown on the table as ΔE (mV) between an aqueous 0.15M NaCl solution and 6.9 U/ml heparin in an aqueous solution of 0.15M NaCl. Table III demonstrates that significant potentiometric responses can be achieved with various quaternary ammonium salts. Excellent response was achieved with membranes (j) and (k).

TABLE III

POTENTIOMETRIC RESPONSE TO HEPARIN AND COMPOSITIONS OF MEMBRANES COMPOSED OF 66 MG PVC, ~132 MG DOS AND 6 MG QUATERNARY AMMONIUM SALT

| Membrane | ΔE 0–6.9 U/ml (in 0.15M NaCl) | 4° ammonium salt | 66 mg PVC (wt %) | mg of DOS (wt %) | 6 mg of 4° salt (wt %) |
|---|---|---|---|---|---|
| a | −3.6 | Triethyl phenyl ammonium iodide | (32.31) | 132.6 (64.90) | (2.94) |
| b | −4.4 | Tetrapentyl ammonium bromide | (32.12) | 133.5 (64.96) | (2.92) |
| c | −10.6 | Trimethyl phenyl ammonium | (32.29) | 132.5 (64.77) | (2.94) |
| d | −15.4 | Dimethyl dioctadecyl ammonium bromide | (32.43) | 131.5 (64.62) | (2.95) |
| e | 1.9 | Tetraoctyl-ammonium bromide chloride | (32.32) | 132.2 (64.74) | (2.94) |
| f | −6.6 | Hexadecyl tri-methyl ammonium bromide | (32.31) | 132.3 (64.76) | (2.94) |
| g | 2.1 | Tetraethyl ammonium perchlorate | (32.29) | 132.4 (64.77) | (2.94) |
| h | −17 | Tetramethyl ammonium bromide | (31.59) | 136.9 (65.53) | (2.87) |
| i | −3 | Tetrabutyl ammonium iodide | (32.27) | 132.5 (64.79) | (2.93) |
| j | −43.4 | Tridodecyl methyl ammonium chloride | (32.78) | 135.7 (65.33) | (2.89) |
| k | −40.4 | Trioctyl methyl ammonium chloride | (32.30) | 132.6 (64.80) | (2.90) |

EXAMPLE 4

A heparin-selective polymer membrane electrode made in accordance with the present invention was tested in samples comprising human whole blood. The results are shown on FIG. 5 which is a graphical representation of the response characteristics of the heparin-selective electrode to specimens of undiluted human blood containing different levels of heparin. The potential in mV is plotted against time. For purposes of comparison, a 15 minute increment is marked on the chart.

Figure 5:
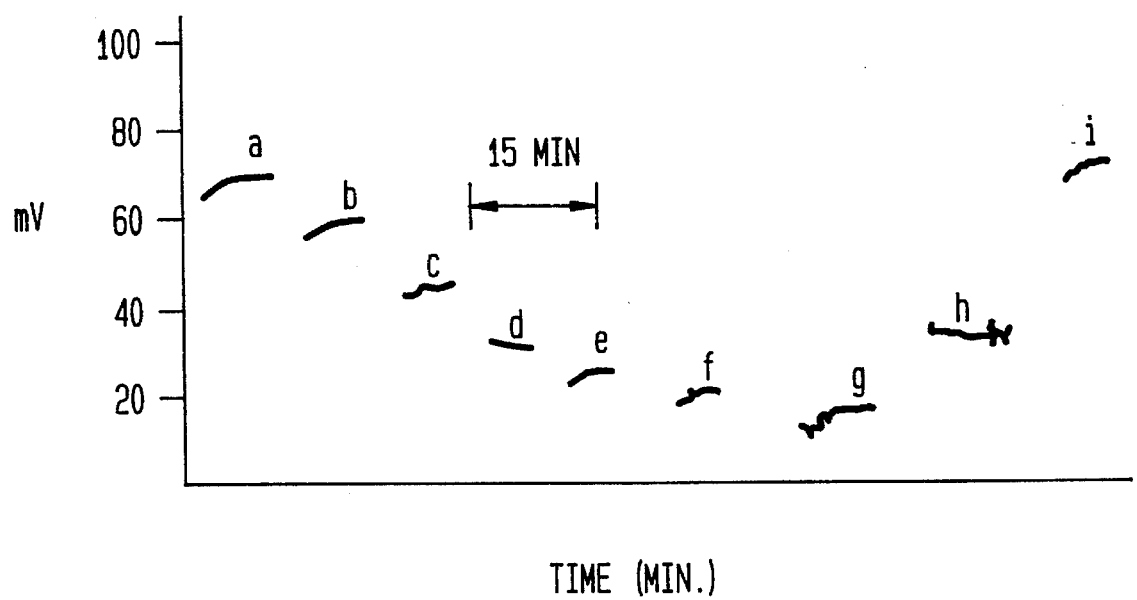
FIG. 5 is a graphical representation of the response characteristics of a heparin-selective electrode to undiluted human blood samples.

The samples, designated by letters (a) to (i), were obtained as clinical specimens from one patient. A quantity of whole blood was withdrawn from the patient and divided into samples having no heparin (a) and heparin in varying added amounts (b) to (g). Then, heparin was administered to the patient and a second specimen (h) was withdrawn for a clinical assessment of heparin concentration in the blood using the heparin-selective polymer membrane electrode of the present invention. Next, protamine was administered to the patient to neutralize the heparin and a third specimen (i) was withdrawn. The sample contents are summarized as follows:

(a) whole blood, no heparin
(b) whole blood, heparin concentration of 1.00 U/ml
(c) whole blood, heparin concentration of 1.58 U/ml
(d) whole blood, heparin concentration of 2.51 U/ml
(e) whole blood, heparin concentration of 3.98 U/ml
(f) whole blood, heparin concentration of 6.31 U/ml
(g) whole blood, heparin concentration of 10 U/ml
(h) whole blood, heparin concentration unknown
(i) whole blood, protamine-neutralized, remaining heparin concentration unknown Referring to FIG. 5, the electrode's response toward heparin in samples (h) and (i) is stable within less than 1 minute. Clotting-time based estimates of the actual heparin content of samples (h) and (i) correlate well with the heparin concentration determined through use of the electrode with a pre-constructed calibration curve.

The wash-out time, or time required for the signal to return to baseline, using a 2M NaCl solution to dissociate the heparin bound to the electrode surface was less than 5 minutes in for the results recorded on FIG. 5. Shorter wash-out times are possible with higher concentration NaCl solutions.

Figure 6:
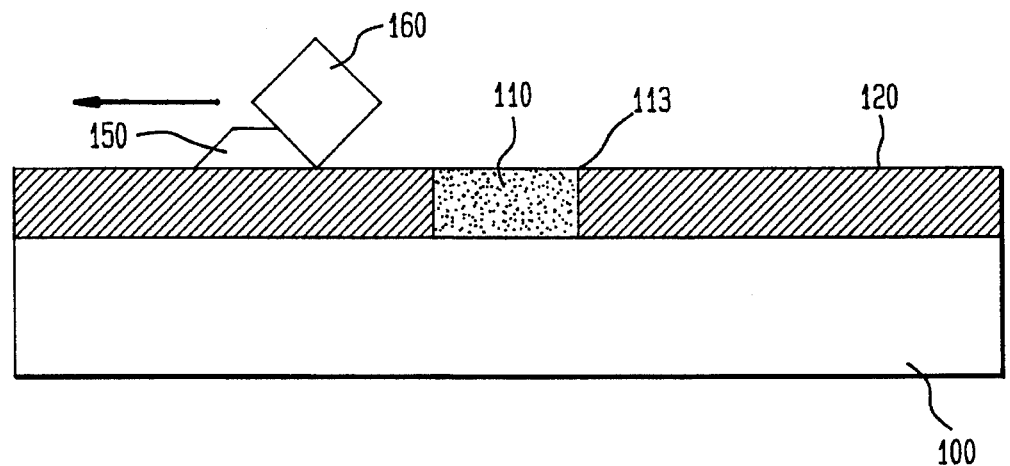
FIG. 6 is a simplified schematic side view which is useful in describing a screen printing process for forming an ion selective membrane.

FIG. 6 is a simplified schematic representation of a silicon wafer upon which is being deposited a polymeric membrane 110. In the practice of the invention, polymeric membrane 110 is ion-selective, as described in the co-pending patent applications which have been incorporated herein.

In the practice of the invention, a mask 120 is installed on silicon wafer 100. The mask has an aperture 113 in which is shown to be deposited the polymeric membrane material. Mask 120 may be formed of a stainless steel mesh coated with a photoreactive emulsion (not shown). Alternatively, the mask may be formed as a metal-foil stencil. In another embodiment, the mask is patterned with the desired features for membrane printing.

A screen printer (not shown) evenly applies the membrane paste, the excess of which is indicated as paste 150, and rubs the paste with a squeegee member 160 which pushes the paste through aperture 113 and onto silicon wafer 100 which functions as a substrate. Squeegee member 160 is, in this embodiment, moved in the direction of the arrow shown in the figure.

As can be seen from this figure, the thickness of polymeric membrane 110 is responsive to the thickness of mask 120. In practical embodiments of the invention, the mask can have a thickness of approximately between 25 microns and 250 microns. A modern, optical-aligned screen printer, such as model LS-15TV which is commercially available from the New Long Seimitsu Kogyo Company, allows alignment and reproducibility to approximately ±5 microns.

The screen printing method of fabricating solid-state ion-selective sensors of the present invention imposes rheological constraints upon the membrane material. Solvents and additives (not shown) are used to form the membrane paste, such as paste 150, having an appropriate viscosity and thixotropy to achieve good pattern definition.

Figure 7:
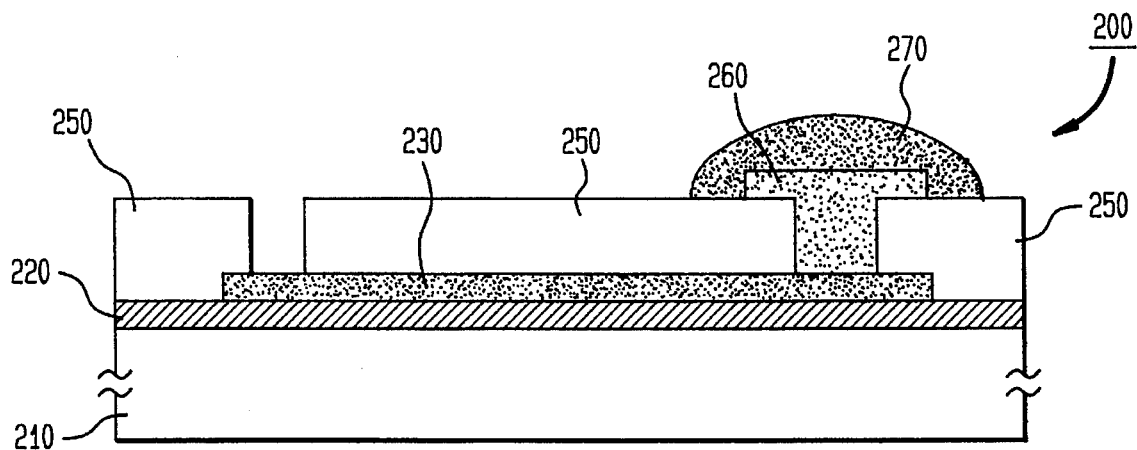
FIG. 7 is a simplified schematic representation of a solid-state microelectrode constructed in accordance with the invention.

The design and configuration of the silicon chip is shown in FIG. 7. The polymer membrane casting solution was made by adding 1.5 wt. % TDMAC directly to a dissolved silicone rubber solution without the addition of a plasticizer. After cleaning the surface of the silicon chip with isopropyl alcohol in a supersonic bath for about 20 minutes, the polymer membrane casting solution was applied on the surface of the silver epoxy site. The surface area of the silver epoxy solid contact was 0.41 mm$^2$, whereas the area of the membrane was about 4.9 mm$^2$ with a thickness of about 150 μm. The emf of the solid-state heparin sensor was monitored in 0.12M NaCl solution by the addition of different concentrations of heparin. Preliminary data demonstrated the feasibility of this embodiment.

Further studies show that the heparin-sensing electrode can be regenerated by rinsing the sensing membrane with 1–2M NaCl solution. It is, therefore, possible to use the electrode in a simple, flow-through arrangement, such as that employed in most currently available ion-analyzers, where automatic rinsing capabilities can be incorporated for continuous regeneration of the sensor.

In an alternate embodiment, a mass-fabricated, solid-state disposable heparin sensor for single use is fabricated by screen-printing a silicone rubber polymer membrane containing the appropriate level of TDMAC (i.e., about 1.5 wt. %) on the surface of a previously designed microelectronic silicone chip of dimension 1 cm×1 cm×0.5 mm. The electrochemical response to heparin was tested in a solution containing 0.12M NaCl and exhibited good correlation to predicted results.

FIG. 7 is a simplified schematic representation of a solid-state microelectrode 200 which was fabricated using the screen printing system of the present invention with CMOS-compatible technology. Solid-state microelectrode 200 is shown to have a silicon substrate 210 with a layer of silicon dioxide 220 thereon. An aluminum electrode 230 is deposited on the silicon dioxide layer and a layer of silicon nitride 250 is arranged over the aluminum electrode and the silicon dioxide layer. A screen printing process similar to that described hereinabove with respect to FIG. 6 was employed to produce a silver epoxy contact 260. The epoxy may be of the type which is commercially available under the brand name Epotek H20E. In addition, a polyurethane-based membrane 270 was also produced using the screen printing process and arranged to overlie the solid silver epoxy contact. Thus, screen printing technology is applicable to the fabrication of the contacts and the membranes.

It is highly desirable that the ion-selective membranes, such as a silicone rubber or -based membrane 270 herein, be of a type which adheres well to silicon-based materials, such as silicon nitride layer 250. Such adhesion reduces the probability that electrolyte shunts will form behind the membrane, rendering the solid-state microelectrode inoperative.

The heparin-selective polymer membrane sensor of the present invention yields fast and reliable potentiometric response to heparin. The dynamic response time is less than 1 minute at clinically important heparin concentrations in undiluted human plasma or blood samples. The return to baseline potential time is less than 5 minutes. Thus, the heparin-selective polymer membrane sensor is suitable for use as a single-use disposable device, or as a more permanent sensor within an instrument-based system wherein the response to heparinized blood can be reversed by flushing with a high concentration salt solution between discrete sample measurements. In certain embodiments, the heparin-selective polymer membrane sensor can be adapted for continuous in vivo sensing.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An ion-selective electrode membrane comprising, in admixture, a polymeric matrix material and an anion exchange material, the electrode membrane admixture being selective to heparin.

2. The electrode membrane of claim 1 wherein the anion exchange material is selected from the group consisting of a quaternary ammonium salts, quaternary phosphonium salts, and quaternary arsonium salts.

3. The electrode membrane of claim 2 wherein the anion exchange material is a quaternary ammonium salt.

4. The electrode membrane of claim 3 wherein the quaternary ammonium salt is selected from the group consisting of triethyl phenyl ammonium iodide, tetrapentyl ammonium bromide, trimethyl phenyl ammonium, dimethyl dioctadecyl ammonium bromide, tetraoctylammonium bromide chloride, hexadecyl trimethyl ammonium bromide, tetraethyl ammonium perchlorate, tetramethyl ammonium bromide, tetrabutyl ammonium iodide, tridodecyl methyl ammonium chloride, polybrene, and trioctyl methyl ammonium chloride.

5. The electrode membrane of claim 4 wherein the quaternary ammonium salt is tridodecyl methyl ammonium chloride.

6. The electrode membrane of claim 1 wherein the polymeric matrix material is silicone rubber.

7. An ion-selective electrode membrane comprising:
   silicone rubber; and
   0.1–12 weight percent tridodecyl methyl ammnonium chloride, the ion-selective electrode membrane being selective for heparin.

8. The ion-selective electrode membrane of claim 7, wherein said tridodecyl methyl ammonium chloride is present preferably in a weight percent of 1.5%.

9. The ion-selective electrode membrane of claim 8, wherein said tridodecyl methyl ammonium chloride is combined with said silicone rubber while said silicone rubber is in a dissolved state.

10. The ion-selective electrode membrane of claim 7, wherein said silicone rubber and said tridodecyl methyl ammonium chloride dissolved therein are installed as a layer on an integrated circuit chip.

11. The ion-selective electrode membrane of claim 10 wherein said silicone rubber and said tridodecyl methyl ammonium chloride is installed by a screen printing process.

12. A method of forming a substance-sensitive membrane for a solid state sensor arrangement, the process comprising the steps of:
   dissolving a silicone rubber solution;
   adding approximately 1.5 weight percent of tridodecyl methyl ammonium chloride to said dissolved silicone rubber solution; and
   applying said silicone rubber solution with tridodecyl methyl ammonium chloride onto a silicon-based integrated circuit chip.

13. The method of claim 12, wherein prior to performing said step of applying, there is provided the further step of cleaning the silicon-based integrated circuit chip in an alcohol bath.

14. The method of claim 13, wherein said alcohol bath is a supersonic alcohol bath.

15. In an integrated circuit chemical sensor arrangement having an input electrode formed of a conductive material in the vicinity of a silicon-based semiconductor material, a permselective membrane having an electrochemical property responsive to heparin and formed of a silicone-based compound arranged to be in adherence with said silicon-based semiconductor material and in electrical communication with said input electrode, for producing at said input electrode a voltage responsive to said electrochemical property.

16. The integrated circuit chemical sensor arrangement of claim 15 wherein said electrochemical property of said permselective membrane results from tridodecyl methyl ammonium chloride distributed throughout said silicone-based compound.

17. An integrated circuit chemical sensor arrangement comprising:
- an input electrode formed of a conductive material in the vicinity of a silicon-based semiconductor material; and
- a permselective membrane having a heparin-selective electrochemical property and formed of a polymeric compound dissolved in a solvent with tridodecyl methyl ammonium chloride, whereby said tridodecyl methyl ammonium chloride is distributed in said polymeric compound, and then removing said solvent, said permselective membrane being arranged to be in adherence with said silicon-based semiconductor material and in electrical communication with said input electrode, for producing at said input electrode a voltage responsive to a concentration of heparin.

18. The integrated circuit chemical sensor arrangement of claim 17, wherein said conductive material is a silver epoxy.

19. The integrated circuit chemical sensor arrangement of claim 18, wherein said silver epoxy forms an electrical contact having a surface area of approximately 0.41 mm$^2$, and said permselective membrane has an area of approximately 5 mm$^2$.

20. The integrated circuit chemical sensor arrangement of claim 18, wherein said permselective membrane has a thickness of approximately 150 μm.

21. The integrated circuit chemical sensor arrangement of claim 18, wherein said permselective membrane is screen printed onto said silicon-based semiconductor material.

\* \* \* \* \*